US009459272B2

(12) United States Patent
Kelso et al.

(10) Patent No.: US 9,459,272 B2
(45) Date of Patent: Oct. 4, 2016

(54) TRANSFER OR INTERROGATION OF MATERIALS BY CARRIER AND RECEIVING DEVICES MOVING INDEPENDENTLY AND SIMULTANEOUSLY ON MULTIPLE AXES

(75) Inventors: Reed Kelso, San Francisco, CA (US); Benjamin Shamah, Palo Alto, CA (US); Tony Lima, Cupertino, CA (US); Eric Rollins, Los Gatos, CA (US); David K. Matsumoto, San Jose, CA (US); Mark Sibenac, Oakland, CA (US)

(73) Assignee: BioNex Solutions, Inc., San Jose, CA (US)

( * ) Notice: Subject to any disclaimer, the term of this patent is extended or adjusted under 35 U.S.C. 154(b) by 408 days.

(21) Appl. No.: 13/636,631

(22) PCT Filed: Mar. 18, 2011

(86) PCT No.: PCT/US2011/029096
§ 371 (c)(1),
(2), (4) Date: Sep. 21, 2012

(87) PCT Pub. No.: WO2011/119441
PCT Pub. Date: Sep. 29, 2011

(65) Prior Publication Data
US 2013/0029856 A1    Jan. 31, 2013

Related U.S. Application Data

(60) Provisional application No. 61/316,236, filed on Mar. 22, 2010.

(51) Int. Cl.
*G01N 35/00* (2006.01)
*G01N 35/02* (2006.01)
(Continued)

(52) U.S. Cl.
CPC ............ *G01N 35/028* (2013.01); *G01N 35/04* (2013.01); *G01N 35/1011* (2013.01); *G01N 2035/0424* (2013.01)

(58) Field of Classification Search
CPC combination set(s) only.
See application file for complete search history.

(56) References Cited

U.S. PATENT DOCUMENTS 7,169,362 B2 * 1/2007 Toi et al. .................. 422/511
7,832,292 B2 * 11/2010 Thomas .................... 73/864.23
(Continued)

FOREIGN PATENT DOCUMENTS

EP         876219      11/1998
EP        1153299      11/2001
(Continued)

OTHER PUBLICATIONS

PCT International Search Report and Written Opinion, PCT Application No. PCT/US2011/029096, May 25, 2011, 12 pages.

*Primary Examiner* — Brian R Gordon
(74) *Attorney, Agent, or Firm* — Fenwick & West LLP

(57) ABSTRACT

Material transfer/interrogation devices (e.g. liquid handling workstations) have been designed in the past for transferring material from a source to a destination location or for interrogating a material at a location, where the locations remain fixed. The invention provides methods and apparatuses for transferring or interrogating materials by one or more carrier devices to one or more receiving devices, where the carrier and receiving devices move independently and simultaneously on multiple axes. In some embodiments, one or more of the carrier and receiving devices can move along an X, Z, Y, and Theta axis, which allows the source and destination locations to rotate and translate relative to each other. Due to this rotation and translation, containers can be positioned to minimize the distance traveled between a pick location from the source and a place location on the destination, greatly increasing the speed at which material transfer can occur.

18 Claims, 12 Drawing Sheets

(51) Int. Cl.
*G01N 35/04* (2006.01)
*G01N 35/10* (2006.01)

(56) References Cited

U.S. PATENT DOCUMENTS

| | | |
|---|---|---|
| 2004/0050866 A1 | 3/2004 | Ingenhoven et al. |
| 2004/0096360 A1* | 5/2004 | Toi et al. .................. 422/63 |
| 2004/0134933 A1 | 7/2004 | Mutz et al. |
| 2005/0092058 A1 | 5/2005 | Ellson et al. |
| 2005/0212869 A1 | 9/2005 | Ellson et al. |
| 2005/0244303 A1 | 11/2005 | Ingenhoven et al. |
| 2006/0071983 A1 | 4/2006 | Stearns et al. |
| 2006/0156797 A1 | 7/2006 | Mutz et al. |
| 2007/0175897 A1 | 8/2007 | Ellson |
| 2008/0173077 A1 | 7/2008 | Ellson et al. |
| 2009/0064519 A1* | 3/2009 | Thomas .................. 33/503 |
| 2009/0235764 A1 | 9/2009 | Ganz et al. |

FOREIGN PATENT DOCUMENTS

| | | |
|---|---|---|
| EP | 1206321 | 5/2002 |
| EP | 1354211 | 10/2003 |
| EP | 1759215 | 7/2007 |
| WO | WO 0253777 | 7/2002 |

* cited by examiner

TRANSFER OR INTERROGATION OF MATERIALS BY CARRIER AND RECEIVING DEVICES MOVING INDEPENDENTLY AND SIMULTANEOUSLY ON MULTIPLE AXES

CROSS-REFERENCE TO RELATED APPLICATIONS

This application claims the benefit of U.S. Provisional Application No. 61/316,236, filed Mar. 22, 2010, which is incorporated by reference in its entirety for all purposes, including any appendices and attachments thereof.

BACKGROUND OF THE INVENTION

1. Field of the Invention

The invention relates to apparatuses and methods for transferring or interrogating materials by carrier devices to receiving devices, where the carrier and receiving devices move independently and simultaneously on multiple axes.

2. Description of the Related Art

Laboratory automation has revolutionized the way experiments are conducted in research and clinical laboratories. Advances in lab automation have taken once laborious, manual processes for preparing, measuring, and moving around samples, and transformed these into rapid, high-throughput mechanisms for experimentation, having an enormous impact on various fields, including genomics and drug discovery. Laboratory automation has become essential for efficient, high-throughput analysis of materials in a short period of time.

Even with the advances made in laboratory automation, automation mechanisms have not kept up with the current drive to analyze and produce data more rapidly. Material transfer in automated laboratory processes is well recognized as the bottleneck unit operation that limits process throughput. Small delays in each of the steps of automated material transfer can lead to substantial overall delays in assays, greatly limiting the number of assays that can be performed per day. On an automation system, the delay in transferring material from a location in one microplate to a location on the opposite side of another microplate may seem small at first. However, when the goal is to screen thousands of samples a day, every second or fraction of a second delay in the process can be crucial. Since the containers or microplates are at fixed locations during a particular assay (except during plate loading and unloading onto the machine), prior art approaches provide little or no way to effectively minimize this travel distance between plates or locations in plates. Further, in many systems that transfer samples between microplates via pipettor tips on an automated pipette arm, those tips move as a single unit with the arm, further limiting the flexibility of the system. If there is only one sample to be aspirated or dispensed at a particular location, the other tips remain inactive, waiting for the one tip to complete its aspirating/dispensing step. Similarly, when one tip must be washed or removed and replaced with a new tip, the other tips attached to the arm must also be positioned at the washing/replacement location, potentially sitting idle during the this process. Every moment that a tip sits idle or waits for completion of a process involving another tip limits the overall speed at which an experiment can be conducted.

Some laboratory systems have developed mechanisms to attempt to gain back some lost time. The BECKMAN COULTER BIOMEK® FX, HAMILTON STAR™, and TECAN EVO™ systems have a carrier arm that can move independently of another carrier arm to individually access a deck of destination plates, but multiple tips are still linked together on each carrier arm. Also, the deck of destination plates remains stationary during the transfer process (except for plate loading and unloading). In the TTP LABTECH MOSQUITO®, a single arm/pipettor tip can move independently to pick and choose from individual wells in plates, but the system does not independently move multiple arms/tips. In the AGILENT TECHNOLOGIES VERTICAL PIPETTING STATION™, the arm with multiple pipettor tips moves independently of the plates, but the plates are only moved vertically on plate shelves. The plates cannot be translated or rotated along a plate deck, and the tips cannot access more than one plate at a time since the system relies on the vertically-aligned plate shelves.

Laboratory automation still has not overcome important bottlenecks, such as those associated with having multiple tips/channels tied together, with having plates at fixed locations on a deck, among others. Currently, there are no existing laboratory automation systems having decoupled linear and rotary axes of movement for the carrier and receiving devices.

SUMMARY OF THE INVENTION

Disclosed herein is an apparatus for transfer of material from a source location to a destination location. The apparatus includes a hub along with carrier devices moveably connected to the hub for transferring the material from the source location to the destination location. A carrier movement mechanism associated with the hub and the carrier devices moves the carrier devices independently from each other along at least two axes. The apparatus also includes at least one receiving device moveably connected to the hub. The receiving device holds a container having either the source location, the destination location, or both. A receiver movement mechanism associated with the hub and the receiving device moves the receiving device independently from the carrier devices along at least two axes. At least one of the axes of the receiving device is a rotation axis. The receiving devices are moved to position the container so that the container can provide the material to or receive the material from one of the carrier devices.

Another embodiment of the invention is a method for transfer of material from a source location to a destination location. The method includes a step of moving at least one receiving device holding a container that contains the source location. The receiving device is moved along at least two axes, where at least one of the axes is a rotation axis. The receiving device is moved to position the source location of the container for the transfer of the material. The method also includes a step of moving one of at least two carrier devices independently from the other carrier device along at least two axes. The carrier device is moved to position the carrier device for acquiring the material from the container, and the carrier device then acquires the material from the source location. The method additionally includes a step of moving at least one receiving device holding a container having the destination location. The receiving device is moved along at least two axes, where at least one of the axes is a rotation axis. The receiving device is moved to position the destination location for receiving the material from the carrier arm. The method also comprises a step of moving the carrier device having acquired the material along at least two axes to position the carrier device for depositing the material in the container, and the carrier device then deposits the material at the destination location.

A further embodiment is an apparatus for interrogation of a material at a location including a hub and carrier devices moveably connected to the hub, where each carrier device has a tip at the distal end that is a sensor for interrogating the material (e.g., collecting measurements, images, etc.). A carrier movement mechanism associated with the hub and the carrier devices moves the carrier devices independently from each other along at least two axes. At least one receiving device is moveably connected to the hub for holding a container having the material at the location. A receiver movement mechanism associated with the hub and the receiving device moves the receiving device independently from the carrier devices along at least two axes (including at least one a rotation axis) to position the container to provide the material for interrogation.

An additional embodiment is a method for interrogation of a material at a location. The method includes a step of moving at least one receiving device holding a container having the location along at least two axes, where at least one is a rotation axis, to position the container to provide the material for interrogation. The method also includes moving one of at least two carrier devices independently from the other carrier devices along at least two axes to position a tip of the carrier device into proximity to the material in the container, where the tip is a sensor for interrogating the material. The method further includes interrogating the material, via the tip of the carrier device, at the location.

In a further embodiment, the carrier devices move along the X axis and the Z axis. In an additional embodiment, the receiving devices move along the Y axis and the Theta axis. In a further embodiment, the receiving devices can translate and rotate along a deck or platform of the apparatus independently from and simultaneously with each other and with the carrier devices.

Since the carrier devices and receiving devices can move independently, the apparatus and method can minimize the distance between the source and destination locations, or interrogation locations, during a laboratory experiment to reduce the amount of time it takes to execute transfer or interrogation tasks. This approach can be applied to multiple source and destination locations and can include multiple robotic arms and tips executing the pick and place tasks simultaneously with the goal of minimizing the amount of time it takes to transfer material between source and destination locations. The small amount of time saved with each material transfer between locations leads to a significant amount of time saved overall, and a substantial increase in the speed and efficiency at which experiments can be conducted using the invention. Furthermore, the infinite degrees of rotation of the receiving devices along the Theta axis allows the carrier devices to access the receiving devices in either the landscape or portrait orientation, allows off-center access in a microwell, among other advantages, all of which serve to further increase throughput.

BRIEF DESCRIPTION OF THE DRAWINGS

These and other features, aspects, and advantages of the present invention will become better understood with regard to the following description, and accompanying drawings, where.

The skilled artisan will understand that the drawings are for illustration purposes only. The drawings are not intended to limit the scope of the present teachings in any way.

DETAILED DESCRIPTION OF THE INVENTION

Material Transfer/Interrogation Apparatus

Figure 1:
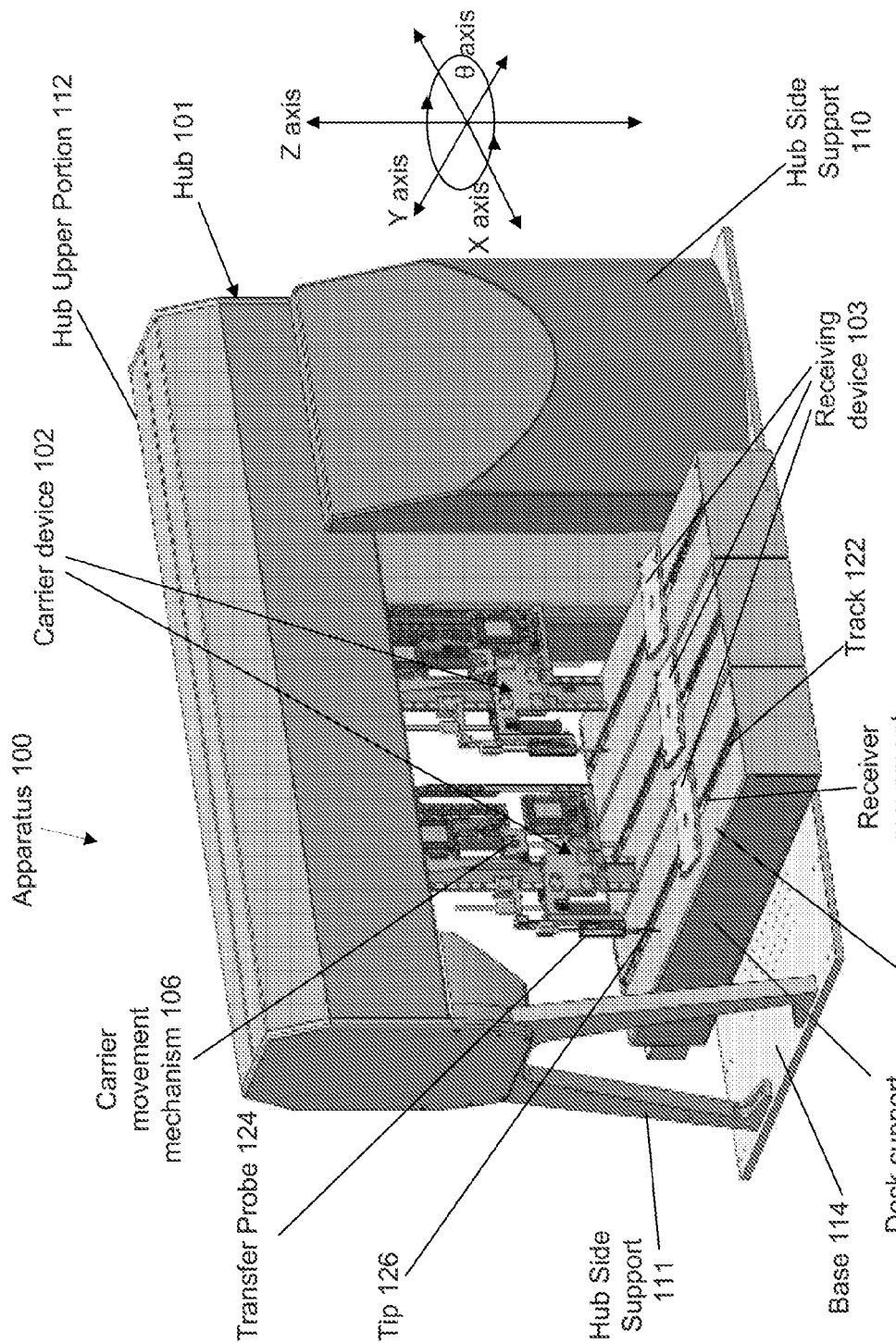
FIG. 1 depicts an isometric view of the apparatus for material transfer or interrogation, according to an embodiment of the invention.

FIG. 1 depicts an isometric view of the apparatus 100 for interrogation of material or transfer of material from a source location to a destination location, according to an embodiment of the invention. The apparatus includes a hub 101 to which the mobile components of the apparatus 100 attach. The hub 101 has a hub upper portion 112 positioned at the top of the hub 101 that is supported by two hub side supports 110, 111. The side supports 110, 111 connect to a base 114 of the hub 101. FIG. 1 illustrates one design of the hub 101, though a variety of other designs are possible. For example, the hub 101 may not contain all of the components mentioned, or they may be positioned differently in the apparatus 100, differently sized or shaped, and so forth.

A deck support 120 rests on the base 114 of the hub 101. The deck support 120 supports a deck 118 or platform on which the experimental analysis occurs. The deck 120 shown in FIG. 1 includes three tracks 122 that run along the length of the deck 118. While three tracks 122 are shown for the purposes of illustration, the number of tracks 122 can vary across different designs of the apparatus 100, from one or two to multiple tracks (e.g., at least 4, 5, 6, 7, 8, 9, 10, 15, 20, or another number of tracks as desired). Similarly, the deck 118 and deck support 120 can be positioned in manners other than those shown in FIG. 1. For example, it could be rotated 90 degrees or could be positioned at an angle relative to the base. The tracks 122 can also be otherwise arranged in the deck 118 (e.g., running perpendicular to the direction shown in the figures, running at an angle, and so forth), and different tracks 122 can be positioned in different ways along the deck. In addition, the tracks do not have to be arranged in a straight line across the deck 118, but could be curved or irregularly shaped.

Three receiving devices 103 are shown in FIG. 1. The receiving devices 103 are moveably connected to the hub 101 for holding a container (not shown in FIG. 1) having a location to be interrogated or to/from which a material transfer can occur. Where a material transfer operation is being performed, the container includes at least one of the source location and the destination location. The source location is a location in the container that will be held by the receiving device 103 from which material will be retrieved or picked up. The destination location is a location in the container at which material will be deposited or released. Where a material interrogation operation is being performed, the container includes a location having material to be analyzed or about which data will be collected. Each receiving device 103 can hold a container, though they do not all have to hold containers at the same time. The source location and destination location can be in two separate containers or in the same container. While three receiving devices 103 are shown in FIG. 1 for the purposes of illustration, the number of receiving devices 103 can vary across different designs of the apparatus 100, from one or two to multiple receiving devices 103 (e.g., at least 4, 5, 6, 7, 8, 9, 10, 15, 20, or another number of devices as desired). FIG. 1 illustrates one receiving device associated with each one of the tracks 122 in the deck 118, though the apparatus 100 could also include more than one receiving device 103 along a track 122, such that there is more than one row of receiving devices 103 (e.g., a second row of receiving devices 103 positioned parallel and adjacent to the illustrated row of receiving devices 103).

Beneath the tracks 122 and contained within the deck support is the receiver movement mechanism 108. The receiver movement mechanism 108 is associated with the hub 101 and with the receiving devices 103 for moving the receiving devices 103 along the tracks 122. The receiver movement mechanism 108 can translate each of the receiving devices 103 by sliding it along the length of the track 122 associated with that receiving device 103. In some embodiments, the receiver movement mechanism 108 is divided into multiple sub-mechanisms such that each receiving device 103 has a separate sub-mechanism associated with it that moves around its respective receiving device 103.

The receiver movement mechanism 108 can also rotate each receiving device 103 by rotation about an axis normal to the plane of the deck 108, such as, e.g., by spinning it around in a circle parallel to the track 122. The receiving devices 103 thus have at least two axes of motion. The devices 103 can move along the Y axis and can also move along a rotational or Theta axis. In some embodiments, the receiver movement mechanism 108 can rotate the receiving devices 103 from 0 degrees to 360 degrees in either direction relative to the carrier devices 102. Each of the receiving devices 103 can be moved independently from and simultaneous with the other receiving devices 103, including translating each device 103 independently and rotating each device 103 independently. Any receiving device 103 can be at any given position along the Y axis or along the Theta axis at any given time, and different devices 103 can be at different positions. The movement of each receiving device 103 allows that device 103, and the container (not shown in FIG. 1) it is holding, to be positioned so that material contained by the container can be transferred between locations within the container, can be transferred to a location in another container, or can be interrogated. In some embodiments, the devices 103 can move along any or all of a Y axis, a Theta axis, an X axis, and a Z axis.

Two carrier devices 102 are illustrated in FIG. 1. These carrier devices 102 are moveably connected to the hub 101 for transferring the material from the source location to the destination location or for interrogating a material at a location. While two carrier devices 102 are shown in FIG. 1 for the purposes of illustration, the number of carrier devices 102 can vary across different designs of the apparatus 100, from one to multiple carrier devices 102 (e.g., at least 3, 4, 5, 6, 7, 8, 9, 10, 15, 20, or another number of devices as desired). Each carrier device 102 has a transfer probe 124 shown at the left side of the carrier device in FIG. 1. Each carrier device 102 can also have a tip 126 attached the transfer probe 124. The tip 126 can be nonremovably fixed to the transfer probe 124 or can be removable and possibly disposable. In one embodiment, the carrier device 102 is a pipettor, where the transfer probe 124 controls the aspiration or dispensing of a liquid. In this embodiment, the tip 126 can be a pipette tip that can be removed and disposed of after each use or after a certain number of uses. In another embodiment, the tip 126 is a sensor for performing an interrogation of material at a location.

Where the tip 126 is a sensor for interrogating the material, the tip 126 can collect various different types of data, measure physical characteristics, record images or perform another analysis on the material. For example, the tip can be various different types of sensors, including an electrochemical sensor, a temperature sensor, a capacitance sensor, a biosensor, a surface plasmon resonance sensor, a conductivity sensor, a calorimeter, a microspectrophotometer sensor, an ionizing radiation sensor, a voltage sensor, a humidity sensor, an electric field sensor, an oxygen sensor, a humidity sensor, an optical sensor, a camera, among others. Where the tip 126 is a sensor, instead of transferring material from locations, the tip 126 can receive instructions to collect information about the material, such as determining the pH of the material in one or more locations (e.g., wells in a microtiter plate), measure the volume of the material at the location, record an image via a camera, and so forth. If there are multiple carrier devices 102 and receiving devices 103, the carrier devices 102 can travel around to various locations in various receiving device 103 and collect particular data about each. In some embodiments, the tip 126 can both interrogate the material and perform a transfer of the material to another location. For example, the tip 126 might first measure a temperature and biological property of a material at a location, and may then transfer a portion of that material to another location. If that other location includes a different material, the tip 126 could collect further data about the mixture, how the components interact, etc.

A carrier movement mechanism 106 is associated with the hub and with the of carrier devices 102 for moving the carrier devices 102. In one embodiment, the carrier movement mechanism 106 is housed in the hub upper portion 112, and is associated with each of the carrier devices 102. In FIG. 1, a portion of the carrier movement mechanism 106 forms a part of each of the carrier devices 102. For example, some or all of the components at the right of each carrier device 102 in FIG. 1 can form a part of the carrier movement mechanism 106. In some embodiments, the carrier movement mechanism 106 is divided into multiple sub-mechanisms such that each carrier device 102 has a separate sub-mechanism associated with it that moves around its respective carrier device 102. The carrier movement mechanism 106 can translate each carrier device 102 by sliding it along the length of hub upper portion 112, so that the device 102 moves in line with the hub upper portion 112 and perpendicular to the tracks 122 below. In some embodiments, the carrier movement mechanism 106 slides the carrier devices 102 along a track contained in the hub upper portion 102. There can be multiple such tracks and each carrier device 102 can slide along its respective track.

In addition to moving the carrier device along the length of the hub upper portion 112, the carrier movement mechanism 106 can also translate the carrier device 102 up and down relative to the hub upper portion 112. Again, the carrier movement mechanism 106 can be divided into multiple submechanisms for translating the carrier device 102 up and down. The carrier devices 102 thus have at least two axes of motion. In some embodiments, the axes are orthogonal to each other. In the embodiment of FIG. 1, the devices 102 can move along the X axis and can also move along the Z axis. In this manner, the carrier device 102 can be moved by the carrier movement mechanism 106 back and forth from receiving device 103 to receiving device 103, and up and down, away from and toward the receiving device 103. The movement along the Z axis allows the tip 126 of the carrier device 102 to be brought into proximity to a container held by the receiving device 103 to insert the tip 126 into the container for withdrawing or depositing material. The carrier movement mechanism 106 can move each of the carrier devices 102 independently from and simultaneously with the other carrier devices 102 and the receiving devices 103, including translating each device 102 independently across the length of the deck 118 and translating each device 102 independently toward and away from the deck 118. Any carrier device 102 can be at any given position along the X axis or along the Z axis at any given time, and different devices 102 can be at different positions. In the example of FIG. 1, the receiving devices 103 move along the Y axis orthogonal to the X and Z axes of movement of the carrier devices 102, and the devices 103 also move along a Theta axis coincident with Z axis of the carrier devices 102. In some embodiments, the devices 102 can move along any or all of an X axis, a Z axis, a Y axis, and a Theta axis.

Figure 2A:
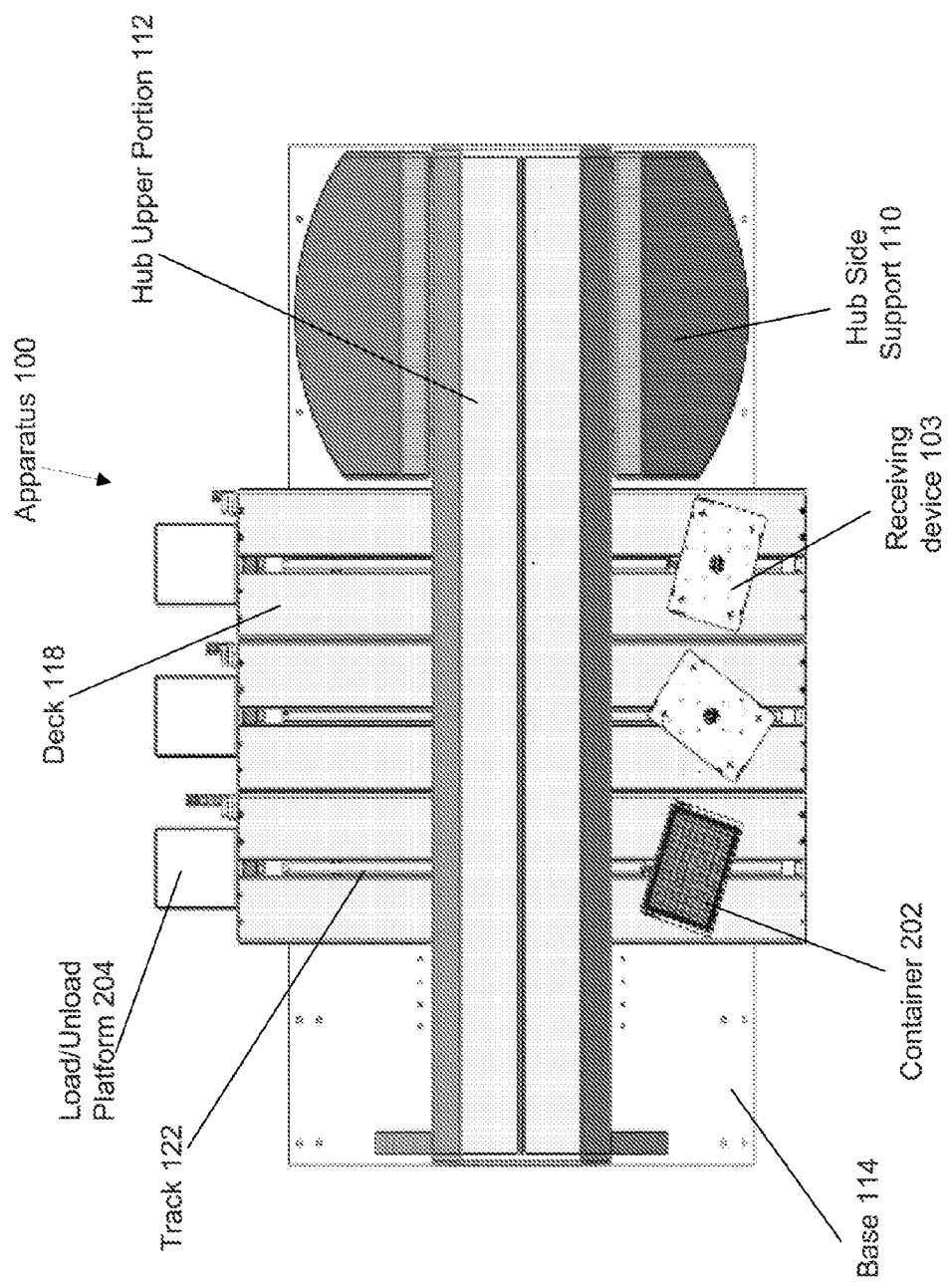
FIG. 2A depicts a top view of the apparatus for material transfer or interrogation, according to an embodiment of the invention.

Referring now to FIG. 2A, there is shown a top view of the apparatus 100 for material transfer or interrogation, according to an embodiment of the invention. FIG. 2A illustrates a top view of the hub upper portion 112 and the hub side support 110 seen in FIG. 1, along with the base 114 on which is positioned the deck 118. The tracks 122 in the deck 118 are also shown from the top view, including the receiving devices 103 associated with each of the tracks. FIG. 2A further illustrates a container 202 on one of the receiving devices 103. In FIG. 2A, the container 202 shown is a microtiter plate or microplate with multiple wells. The container 202 can be a 96-, 384-1536-, 3456-well microtiter plate, or a plate containing some other number of wells. The container 202 can also be another type of container, such as a vial, a tube, a microscope slide, a microarray, a wash container, a pipette tip holder, a Petri dish, and other types of containers.

Various different forms of material can be contained within the container 202, such as a solid, a liquid, a gel, among others. The material can also be various different material types, including genetic material, protein, various organisms (e.g., yeast, bacteria, etc.), reagents and solutions, beads, combinatorial libraries, gels, and so forth. Further, the apparatus 100 can be used for a variety of procedures, experiments, assays, etc., such as high throughput drug screening, compound management, toxicology, dissolution testing, immunoassays, clinical diagnostics, in vitro diagnostics, veterinary diagnostics, nucleic acid extraction, gel electrophoresis, genotyping, DNA extraction, PCR applications, genomics, proteomics, cellomics, cell biology, metabolomics, molecular biology, in vitro diagnostics, toxicology, microarray spotting, forensics, food analysis, colony picking, gel cutting, solubility assays, among a variety of others.

Though only one container 202 is illustrated in FIG. 2A, each receiving device 103 can hold a container. The containers 202 held by each receiving device 103 can be the same or different containers. The containers 202 can also be the same type, but have different numbers of locations for holding material (e.g., one 384-well microplate and one 1536-well microplate). The carrier devices 102 can transfer material between or collect information in any of these containers. The carrier devices 102 can transfer material between locations in the container 202 (e.g., from well A1 to well B2 in a Microplate A) or between locations in two different containers 202 (e.g., from well C3 in Microplate A to well D5 in Microplate B). FIG. 2A further illustrates a load and unload platform 204. The receiving devices 103 can slide along the deck 118 to the platform 204 at which a container loader can place containers 202 onto the receiving devices 103 and remove containers 202 from the receiving devices 103, as needed. Containers 202 can be loaded/unloaded rapidly (e.g., at least every 1, 3, 5, 10, 15, 20, 30 seconds per container).

Figure 2B:
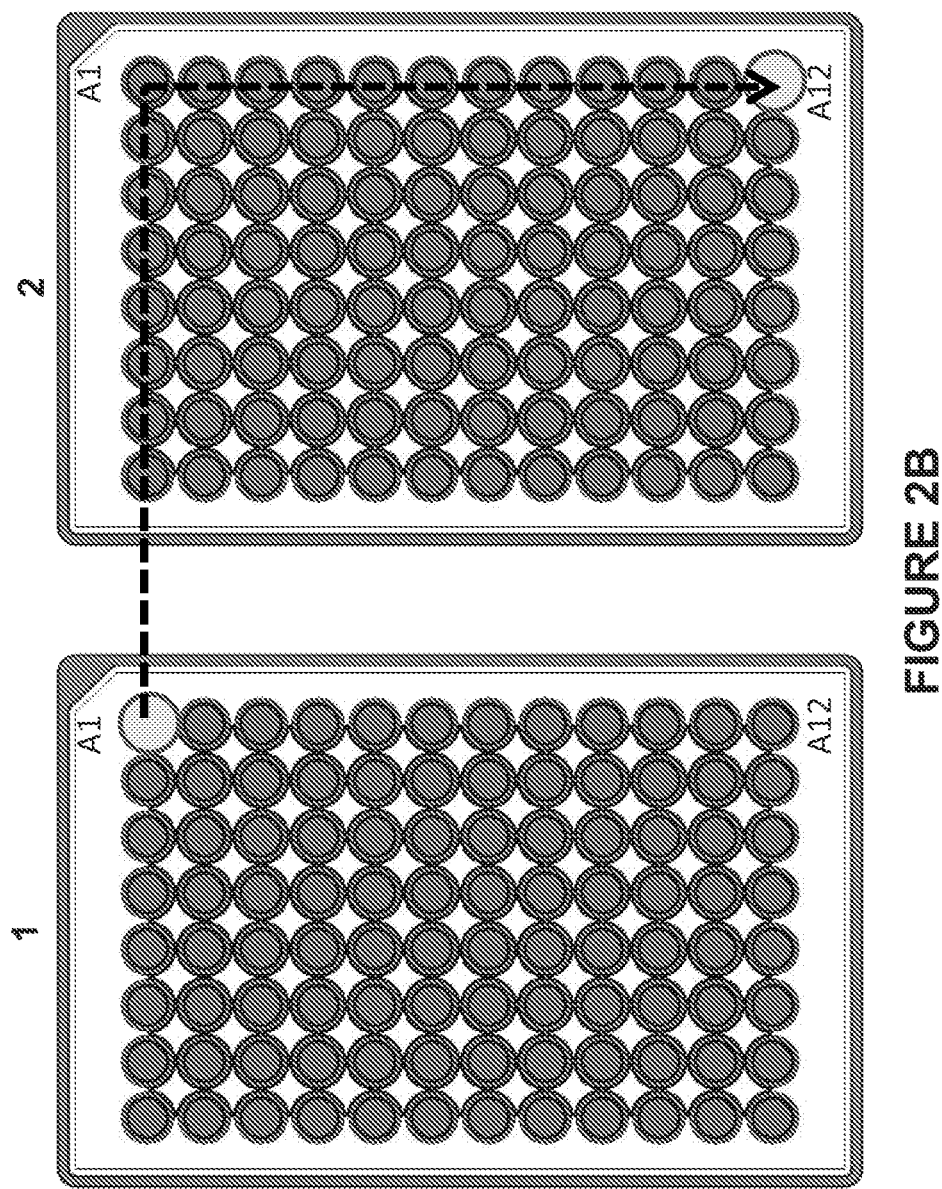
FIG. 2B depicts two microplates lined up side-by-side, as they might be with standard laboratory automation during a material transfer operation.
Figure 2C:
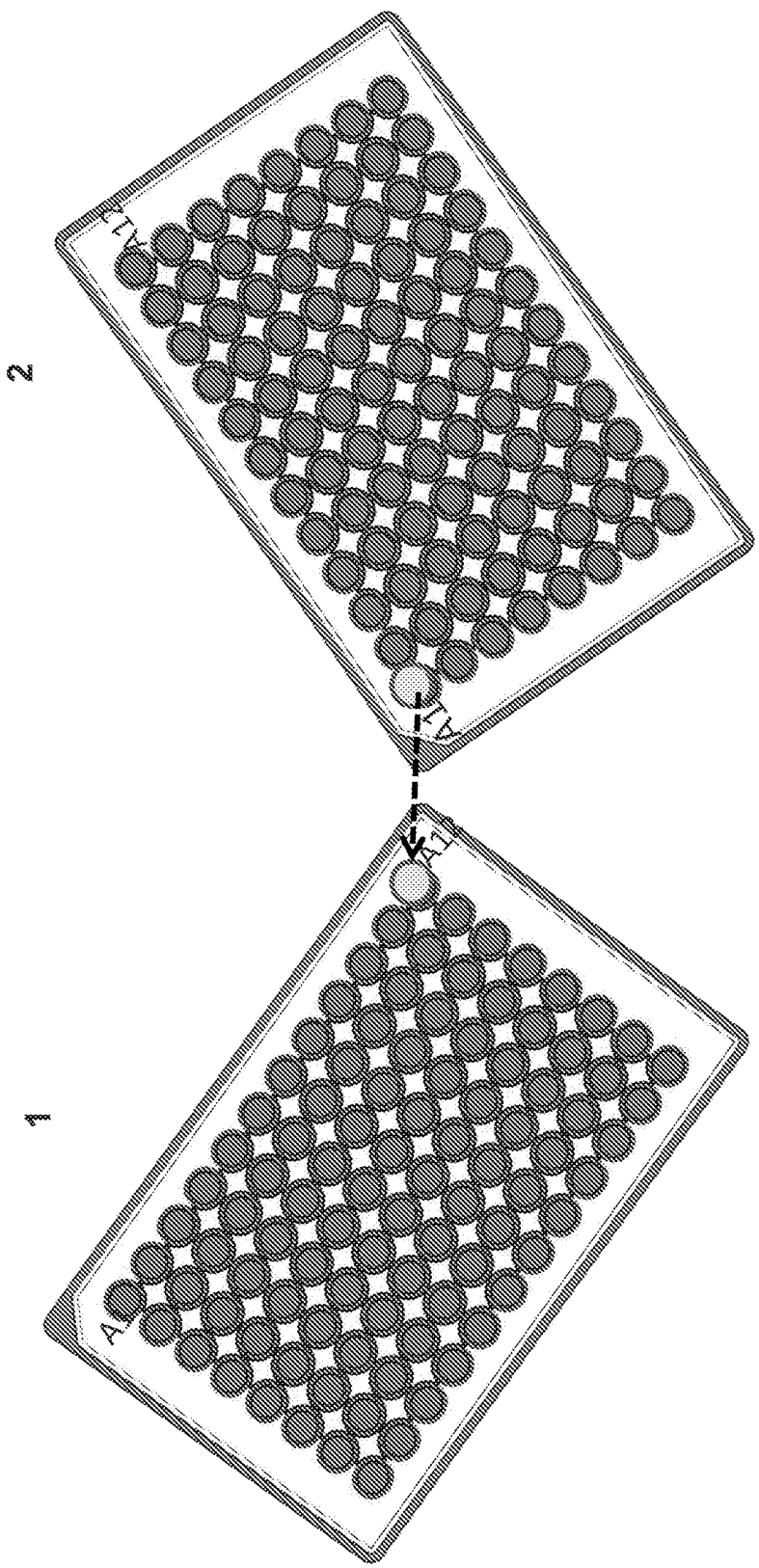
FIG. 2C depicts two microplates positioned next to each other after one has been rotated by the laboratory automation of the invention during a material transfer or interrogation operation, according to an embodiment of the invention.

Since the receiving devices 103 can both translate and rotate along the deck 118, the containers 202 can be positioned as needed for material transfer or interrogation. As a first example, there could be an experiment in which sample from well A1 (source location) of Microplate 1 is to be transferred to well A12 (destination location) of Microplate 2. FIG. 2B illustrates these two microplates lined up side-by-side as they might be on a laboratory automation system without the features of apparatus 100 that allow the plates to be rotated to position the source and destination locations as close together as possible. To retrieve a sample from well A1 of Microplate 1 and transfer it to well A12 of Microplate 2, the carrier mechanism must travel along two axes, as illustrated by the dashed line. FIG. 2C illustrates the same two microplates rotated as they might be on the apparatus 100. The receiver movement mechanism 108 can rotate either microplate (or both microplates) in either direction to arrange well A12 of Microplate 2 as close to well A1 of Microplate 1 as possible. In this case, to retrieve the sample from well A1 of Microplate 1 and transfer it to well A12 of Microplate 2, the carrier mechanism only needs to travel along one axis from the source to the destination location, a shorter distance than in FIG. 2B as illustrated by the dashed line.

Figure 2D:
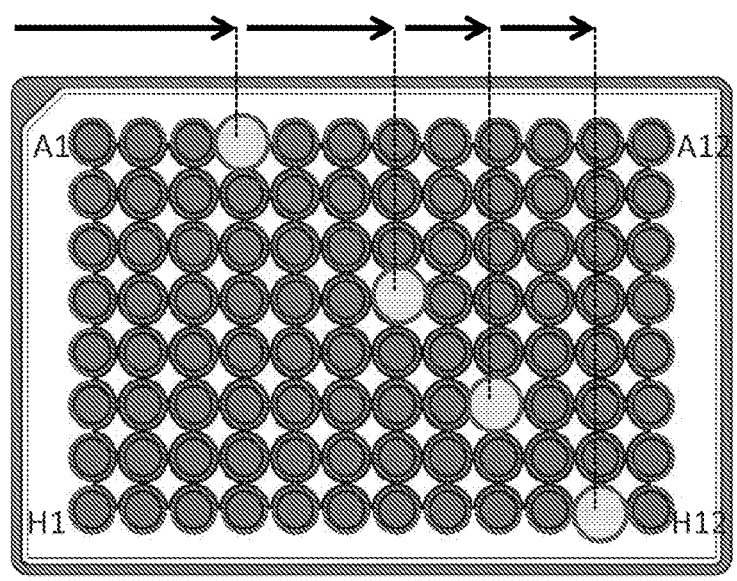
FIG. 2D depicts a microplate as it might be positioned with standard laboratory automation during a material transfer so the picks or transfers in different columns occur sequentially as the carrier travels along the X axis.
Figure 2E:
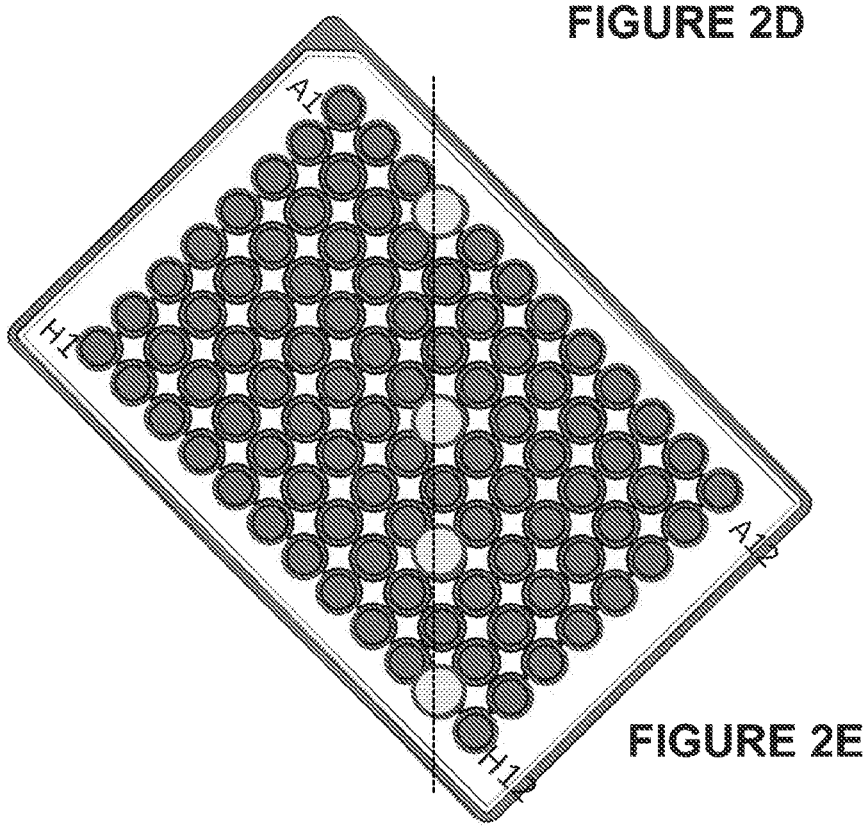
FIG. 2E depicts a microplate that has been rotated via the laboratory automation of the invention to align wells in different columns vertically to allow picks or transfer to occur simultaneously in a single step, according to an embodiment of the invention.

As a second example, there could be an experiment in which samples from various wells across a diagonal of a microplate need to be picked or transferred. FIG. 2D depicts such a microplate as it might be positioned with standard laboratory automation during a material transfer operation so the picks or transfers, or interrogations, in different columns occur sequentially as the carrier travels along the X axis. The carrier has to travel up and down the X axis multiple times to reach all four wells. FIG. 2E depicts a microplate that has been rotated via the laboratory automation of the invention to align wells in different columns vertically to allow picks or transfer to occur simultaneously in a single step. The carrier device 102 only has to travel along the X axis once to reach all four wells since the plate has been rotated to line up the wells according to the direction of travel of the carrier device 102.

Figure 2F:
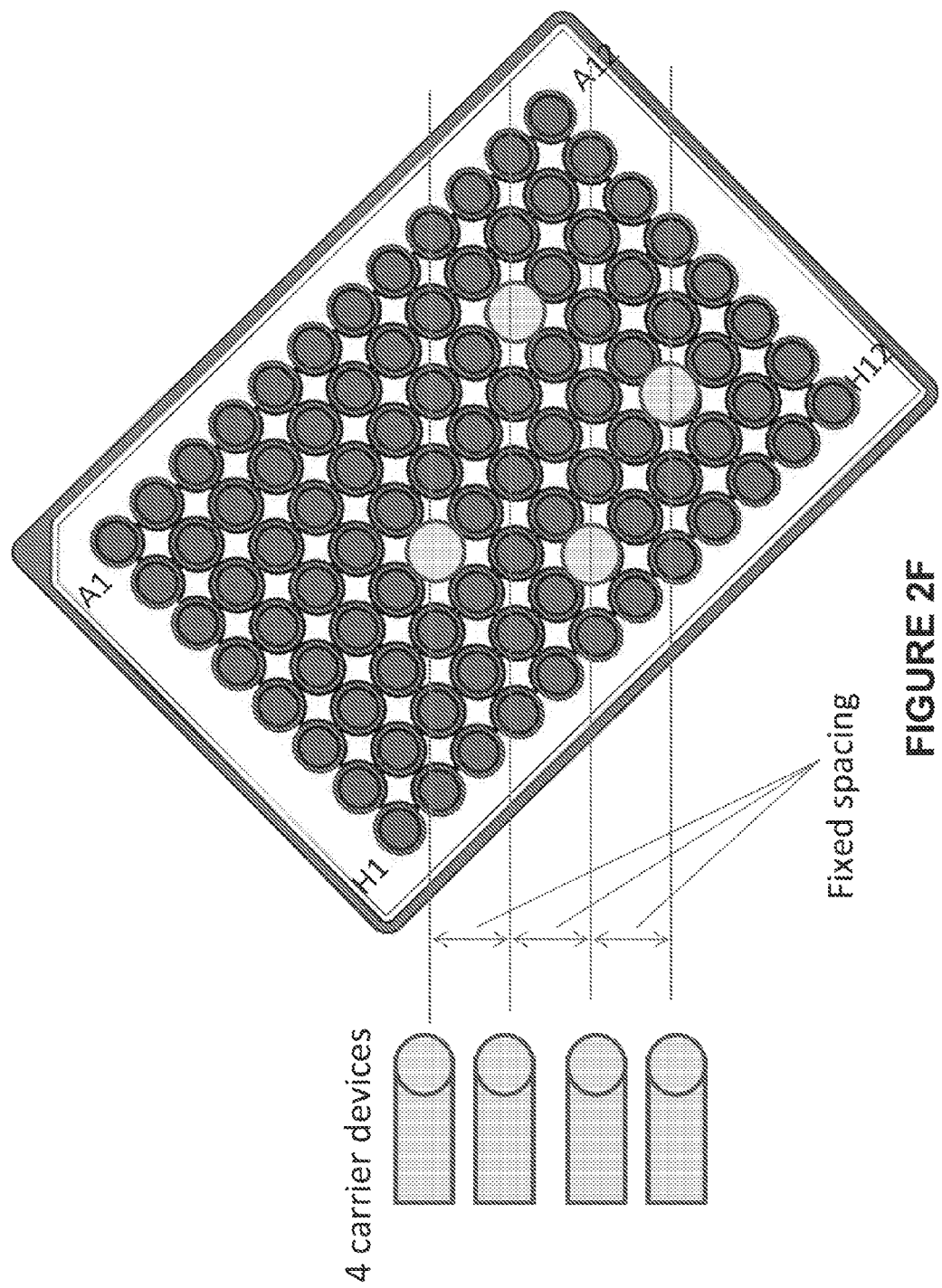
FIG. 2F depicts a microplate that has been rotated via the automation of the invention to align wells to the fixed spacing of the carrier devices, according to an embodiment of the invention.

As a third example, where two or more of the carrier devices 102 are at a fixed spacing, the rotation can effectively change the distance between the wells to match the carrier device 102 spacing. FIG. 2F depicts a microplate that has been rotated to allow simultaneous access to the microplate wells.

Though this rotational repositioning of the well(s) in the microplates of FIGS. 2C, 2E and 2F may only save a few seconds or fractions of seconds of time, over the course of a lengthy experiment or a day's worth of experiments, this can save a significant amount of time. Where there are multiple microplates, they can all be rotating in different directions simultaneously to minimize travel distance for the carrier devices 102 as samples are transferred. In addition, the microplates can be rotating while they are being translated across the deck 118 and while the carrier device 102 is retrieving/releasing/interrogating sample to further save time so the carrier device 102 does not have to wait until the rotation is finished. The tip can also be retrieving/depositing/interrogating sample even if it is off-center at a location or in a well, allowing more flexibility in sample retrieval/interrogation and allowing the carrier device 120 to retrieve/interrogate samples even from very small, densely-arranged locations.

Figure 3:
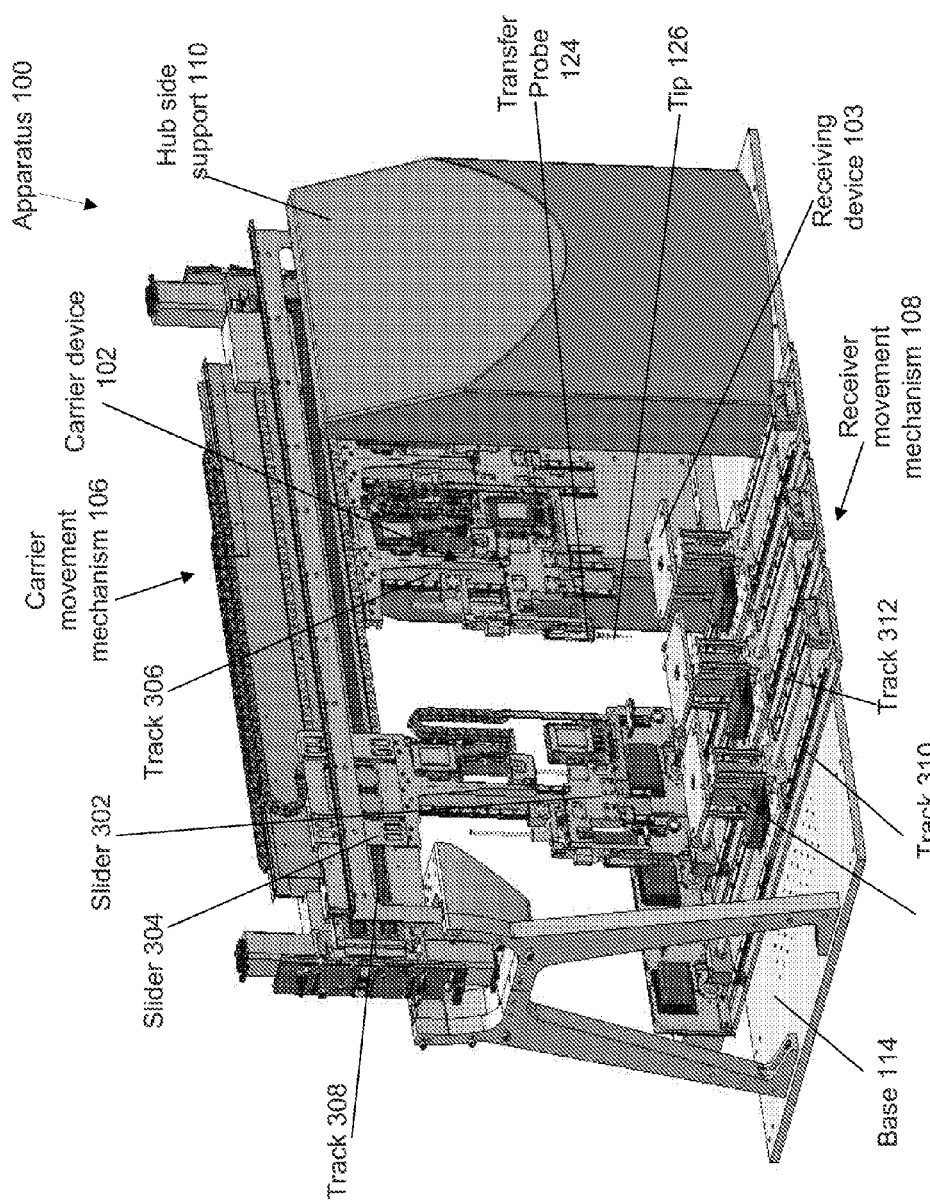
FIG. 3 depicts an isometric view of the apparatus for material transfer or interrogation including the receiver movement mechanism and carrier movement mechanism exposed, according to an embodiment of the invention.

Referring now to FIG. 3, there is shown an isometric view of the apparatus 100 for material transfer or interrogation including the receiver movement mechanism 108 and carrier movement mechanism 106 exposed, according to an embodiment of the invention. The carrier movement mechanism 106 comprises a variety of components, including tracks 306, 308 and sliders 302, 304. Slider 304 is movably attached to a track 308 of the hub and connected to the carrier device. The slider 304 slides the carrier device 102 along track 308 to translate the devices 102 from inside the hub side support 110 across the deck 118 and back. The slider 304 moves the carrier devices 102 along the X axis to position the carrier devices 102 in proximity to the receiving devices 103. There can be multiple tracks 308 and each carrier device 102 can slide along its respective track directly next to the other carrier devices 102. The carrier movement mechanism 106 also includes slider 302 connected to the track 306 of the carrier device 102 and attached to the transfer probe 124. This slider 302 slides the transfer probe 124 of the carrier device 102 up and down along track 306, and so translates the transfer probe 124 closer to and away from the receiving devices 103. The slider 302 moves the transfer probe 124 along a Z axis so that the tip 126 of the transfer probe 124 can be moved down to the container 202 to access the source or destination location. FIG. 3 illustrates just one design for a carrier movement mechanism 106, but other designs or configurations of the components are also possible.

Since there are multiple carrier devices 102 moving independently and simultaneously, the tips 126 can hit multiple locations across multiple receiving devices 103 at a time (e.g., at least 2, 3, 4, 5, 6, 7, 8, 9, 10, 11, 12, 13, 14, 15, 16, 17, 18, 19, 20, etc. points in space at a time). Further, any of the tips 126 can be at any state of the aspiration process (e.g., changing tips, washing tips, aspirating, dispensing, traveling, interrogating, etc.). Thus, one tip 126 is never impeding another tip 126 from finishing a cycle since they are not dependent on each other. In some embodiments, the apparatus 100 can do multiple thousands of fully automated (without requiring user manipulation) material transfers (or material interrogations) a day (e.g., at least 2,000, 3,000, 4,000, 5,000, 6,000, 7,000, 8,000, 9,000, 10,000, 13,000, 15,000, 17,000, 20,000, 25,000, 30,000, 35,000, 40,000, 45,000, 50,000 in an eight-hour time period, or any numbers in between these numbers and any ranges including or between these numbers). The user can thus run an entire experiment in a day.

The transfer probe 124 can be constructed in a variety of ways. For example, the transfer probe 124 can be an aspirator and a dispenser for aspirating/dispensing liquid to/from the container 202. The aspirator/dispenser can be a piston-type aspirator/dispenser, an air displacement aspirator/dispenser, an acoustic aspirator/dispenser, and so forth. The aspirator can also include multiple pin tool components. In one embodiment, the transfer probe 124 comprises a liquid aspirator/dispenser constructed similar to a pipettor device, and the transfer probe 124 has a removable or fixed pipette tip 126 for aspirating the liquid from a well in a first microtiter plate and dispensing the liquid into a well in a second microtiter plate.

FIG. 3 also illustrates the receiver movement mechanism 108 that was hidden under the deck 118 and deck support 120 in FIG. 1. The receiving devices 103 slide along tracks 310 and 312 to translate across the deck 118. A rotator 314 rotates the receiving devices 103 from 0 to 360 degrees in either direction.

Figure 4:
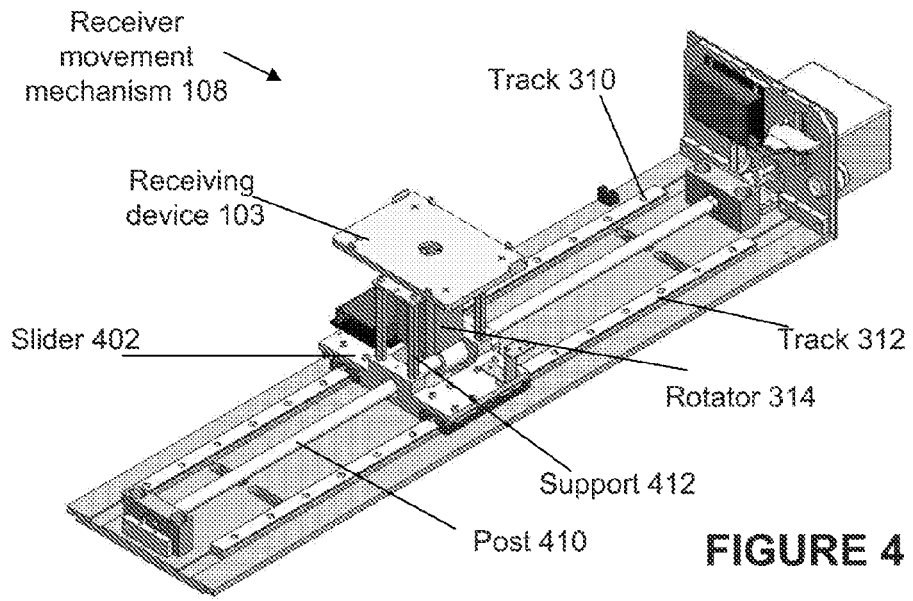
FIG. 4 depicts an isometric view of the receiver movement mechanism separate from the apparatus, according to an embodiment of the invention.

Referring now to FIG. 4, there is shown an isometric view of the receiver movement mechanism 108 separate from the apparatus 100, according to an embodiment of the invention. Tracks 310, 312 are again illustrated, and a slider 402 slides the receiving device 103 along the tracks 310, 312 to translate the receiving device 103 across the deck 118 of the apparatus 100 along the Y axis and into proximity to the carrier devices 102. A post 410 is located between the tracks 310, 312, and the post 410 runs through the slider 402 as it slides along. A support 412 having multiple legs stabilizes the receiving device 103 above the rotator 314 so the rotator 314 can rotate the receiving device 103 around as it translates on the tracks 310, 312. FIGS. 3 and 4 illustrate just one design for a receiver movement mechanism 108, but other designs or configurations of the components are also possible.

Figure 5:
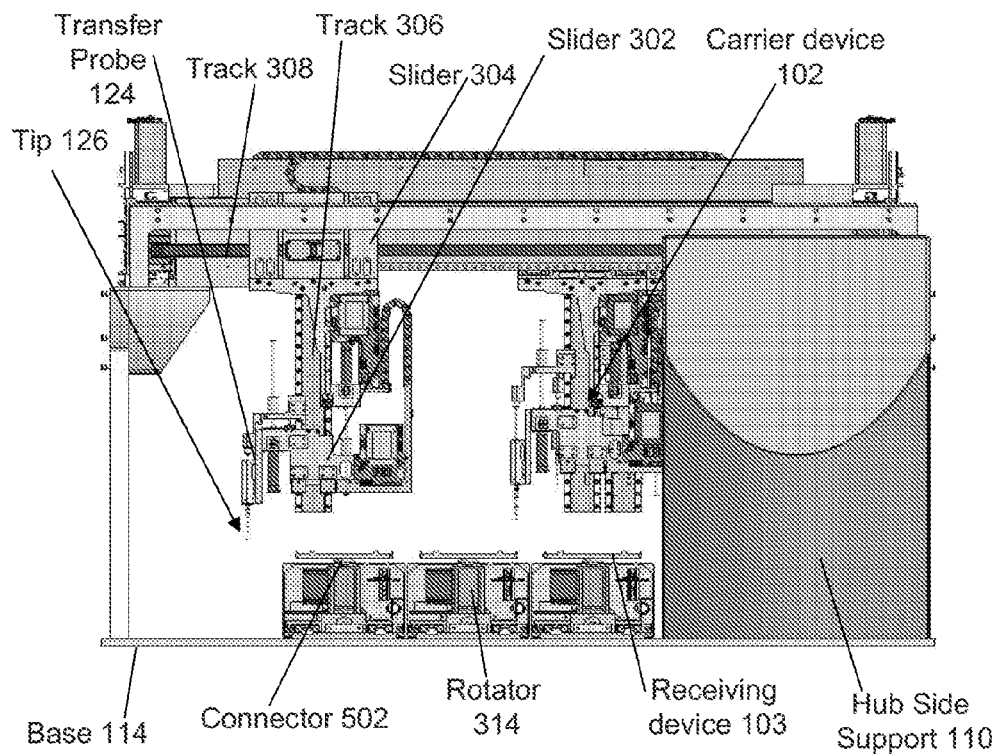
FIG. 5 depicts a front view of the apparatus for material transfer or interrogation including the receiver movement mechanism and carrier movement mechanism exposed, according to an embodiment of the invention.

Referring now to FIG. 5, there is shown a front view of the apparatus for material transfer or interrogation including the receiver movement mechanism 108 and carrier movement mechanism 106 exposed, according to an embodiment of the invention. FIG. 5 further illustrates a connector 502 for connecting the receiver movement mechanism 108, under the deck 118 through an opening or track 122 in the deck to the receiving device 103 above the deck 118 on one of the tracks 112. FIG. 5 also illustrates how the rotator 314 connects to the receiving device 103 via the connector 502 for rotating the device.

The apparatus 100 or certain components of the apparatus 100 can be operated by a computer system including a microcontroller and an application for managing the components and for designing experiments. A user can use an interface associated with the computer system to enter in the instructions for the experiment to be performed, and design the experiment according to the user's needs. For example, the user can specify the types of containers 202 being used (e.g., a 384-well or 1536-well microplate), which locations (e.g., wells) in the containers 202 contain the sample to be analyzed, what reagents in which locations should be combined with other reagents, what type of assay is to be performed, specific time settings needed for the assay, particular interrogations to perform, etc. The computer system can also apply a various algorithms to design the experiment to ensure the most efficiency and speed. For example, the experiment can be organized so that no carrier device 102 is sitting idle other than for brief periods of time. Similarly, containers can be constantly loaded and unloaded from receiving devices 103, and the receiving devices 103 can be constantly translating and rotating around into the most convenient position for the carrier device 102 to access the proper location in the container 202. The computer system can provide instructions to the apparatus 100 accordingly, so that the appropriate receiving devices 103 move to the correct locations on the deck 118 when needed and the appropriate carrier devices 102 move as needed to transfer samples between locations in the receiving devices 103.

The apparatus 100 is further highly customizable to include the number of carrier devices 102 and the number of receiving devices 103 desired by the user of the apparatus 100. Similarly, the components of the apparatus 100 can be modified in shape or size, or rearranged in the apparatus 100 as desired by the user, as needed to better fit into a particular laboratory design or with other machinery in the laboratory, and so forth. In addition, multiple apparatuses 100 can be arranged adjacent to one another and operate in conjunction to conduct multiple different experiments or assays.

FIGS. 1-5 illustrate a possible design for the apparatus. However, one of ordinary skill in the relevant art will recognize that a wide variety of other designs are also possible. Thus, FIGS. 1-5 are provided as illustrations of possible embodiments of the claimed invention.

Material Transfer/Interrogation Methods

Figure 6:
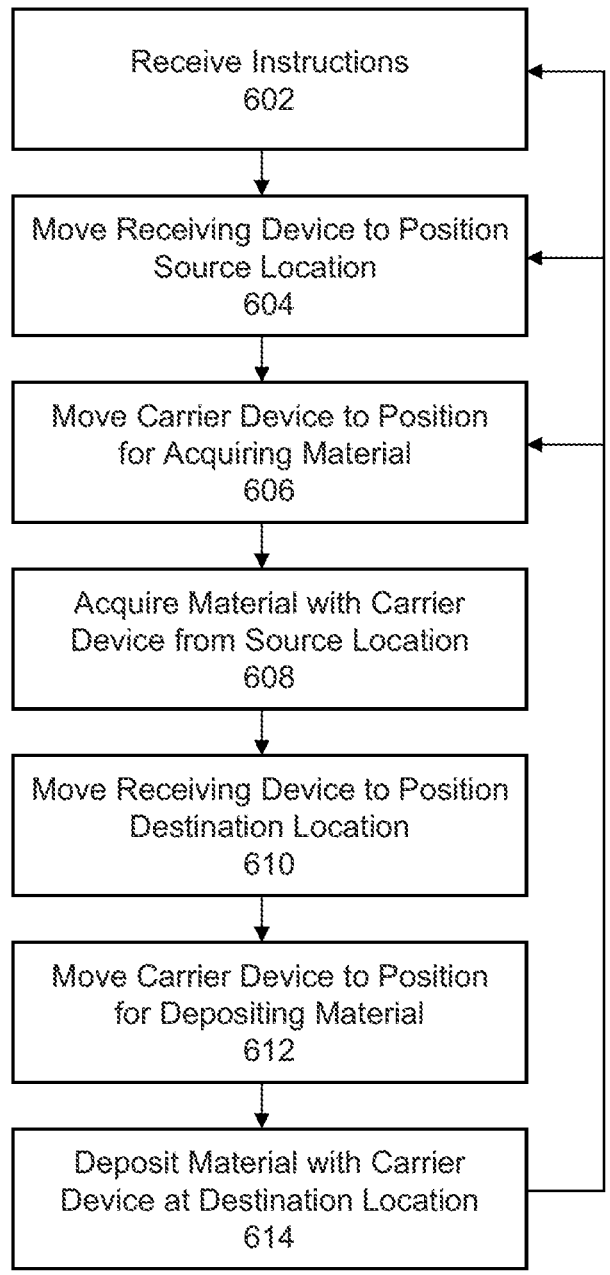
FIG. 6 is a flow diagram providing a method for material transfer, according to an embodiment of the invention.

Referring now to FIG. 6, there is shown a flow diagram providing a method for material transfer, according to an embodiment of the invention. It should be understood that these steps are illustrative only. Different embodiments of the invention may perform the illustrated steps in different orders, omit certain steps, and/or perform additional steps not shown in FIG. 6 (the same is true for FIGS. 7, 8, and 9). The method can start and end at various points in the material transfer process, and typically is a continuous process with multiple steps occurring simultaneously, so FIGS. 6, 7, 8 and 9 provide only an example of one ordering of method steps. In addition, the method can be performed using apparatus 100 or another apparatus capable of performing the steps provided below.

As shown in FIG. 6, the method includes a step of receiving 602 instructions for performing an experiment involving transferring a material from a source location to a destination location. The instructions can be received from a microcontroller or computer system managing the method of material transfer. Based on these instructions, various devices 102, 103 are moved around to transfer the material. Specifically, the method further includes moving 604 at least one receiving device 103 (e.g., a first receiving device) holding a container 202 (e.g., a first container) having the source location along at least two axes (e.g., a Y axis and a Theta axis). The device 103 is moved 604 to properly position the source location for the transfer of the material.

In addition, the method includes moving 606 a carrier device 102 independently from one or more other carrier devices 102 along at least two axes to position the carrier device 102 for acquiring the material. In one embodiment, the at least two axes of the carrier devices are orthogonal to each other (e.g., an X axis and a Z axis).

The method further includes acquiring 608 the material (e.g., aspirating a liquid, etc.), via the carrier device 102, from the source location in the container 202 held by the receiving device 103. The method also includes moving 610 at least one receiving device 103 holding a container that has the destination location. This can be the same, first receiving device/container moved 604 or a different, second receiving device/second container. The device 103 can be moved along at least two axes (e.g., Y and Theta axis), to position the destination location for receiving the material. Additionally, the method includes moving 612 the carrier device 102 that acquired the material along at least two axes to position the carrier device 102 for depositing the material, and depositing 614 the material (e.g., dispensing a liquid) at the destination location. The method can then start over with receiving 602 new instructions or moving 604, 606 devices 102, 103 to continue the experiment.

In the various moving steps 604, 606, 610, 612, the devices 102, 103 can be moved independently of and simultaneously with one another. Further, the steps of acquiring 608 and depositing 614 the material can also occur while the device 103 is rotating. Each step of acquiring 608 and depositing 614 material can occur rapidly (e.g., a fraction of a second, 1, 2, 3, 4, 5, 6 seconds or less, etc., or any ranges including or between these numbers (e.g., 5 seconds or less), or any numbers or fractional numbers in between, etc.). In addition, steps 602-614 can be considered a single transfer, and in some cases, the method includes performing at least 50,000 transfers (e.g., 50,000, 55,000, 60,000, 65,000, 70,000, 75,000, 80,000, 85,000, 90,000, 95,000, 100,000, 150,000, 200,000 transfers, etc., or any ranges including or between these numbers, or any numbers or fractional numbers in between or above) in eight hours or less (e.g., 8, 7, 6, 5, 4, 3, 2, 1 hour(s), 50 minutes, 25 minutes, etc., or any ranges including or between these numbers, or any numbers or fractional numbers in between or below). Further, any of steps 604-614 can be repeated, multiple times, independently and simultaneously at various locations with various devices 102, 103.

Figure 7:
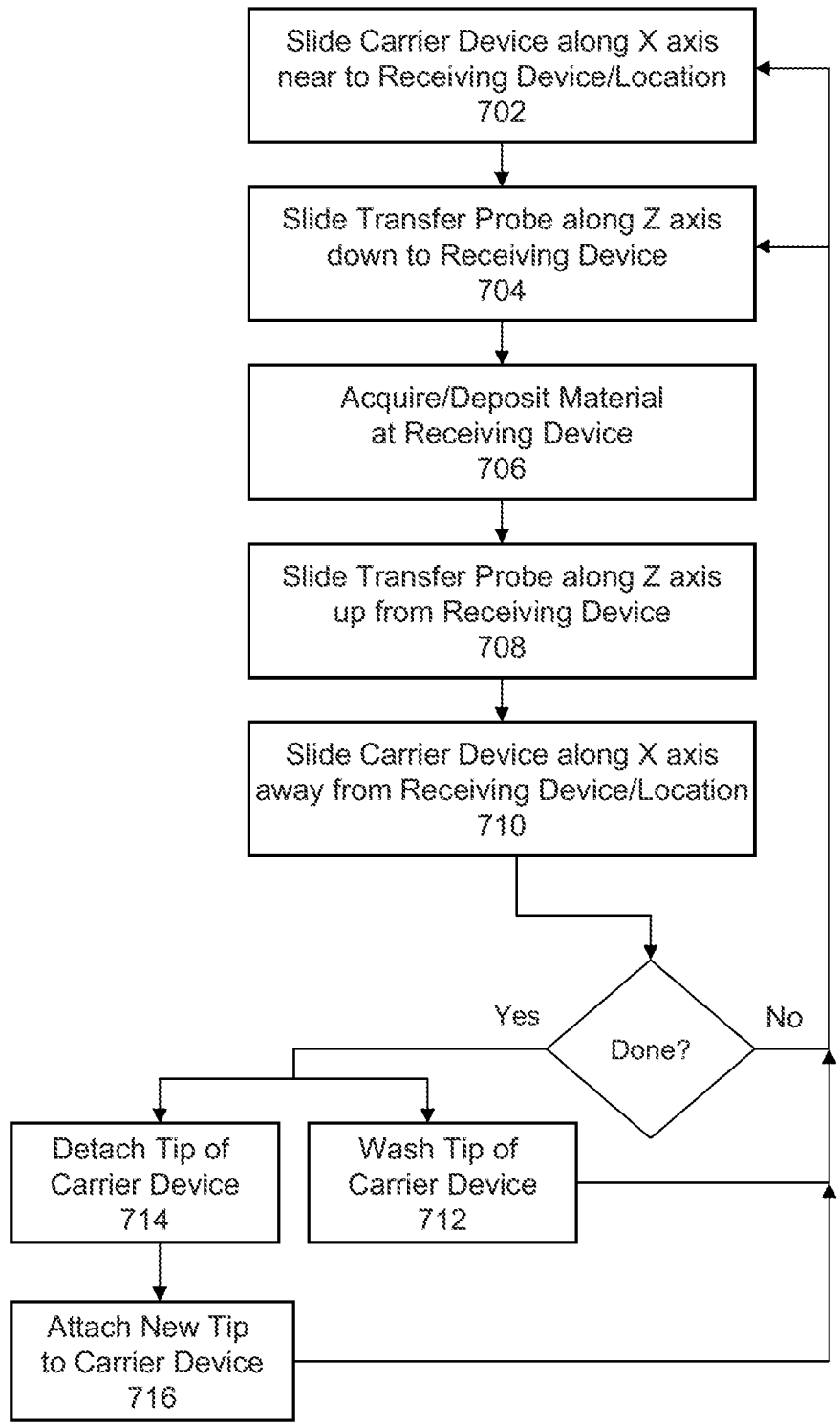
FIG. 7 is a flow diagram providing the method for movement the receiving devices of FIG. 6 in more detail, according to an embodiment of the invention.

Referring now to FIG. 7, there is shown a flow diagram illustrating the moving 606, 612 of the carrier devices 102 in more detail, according to an embodiment of the invention. The method comprises sliding 702 the carrier device 102 along an X axis to position the carrier device 102 in proximity to the receiving device 103/location in device 103. The method then includes sliding 704 the transfer probe 124 of the carrier device 102 along a Z axis down toward the receiving device 103. Steps 702 and 704 may or may not occur simultaneously. The method next comprises acquiring or depositing 706 the material in the receiving device 103. The method further includes sliding 708 the transfer probe 124 along the Z axis up away from the receiving device 103, and sliding 710 the carrier device 102 along the X axis away from the receiving device 103/location in device 103. Steps 708 and 710 may or may not occur simultaneously. If the carrier device 102 is to move to another receiving device 103 to continue the experimental run, steps 702 or 704 can be repeated to reposition the carrier device 102 for the next action. If the experiment is finished, the method can include either washing 712 the fixed tip 126 or detaching 714 a removable tip and attaching 716 a new tip. Any of steps 702-716 can occur for one carrier device 102 simultaneous with others of these steps being performed by other carrier devices 102

Figure 8:
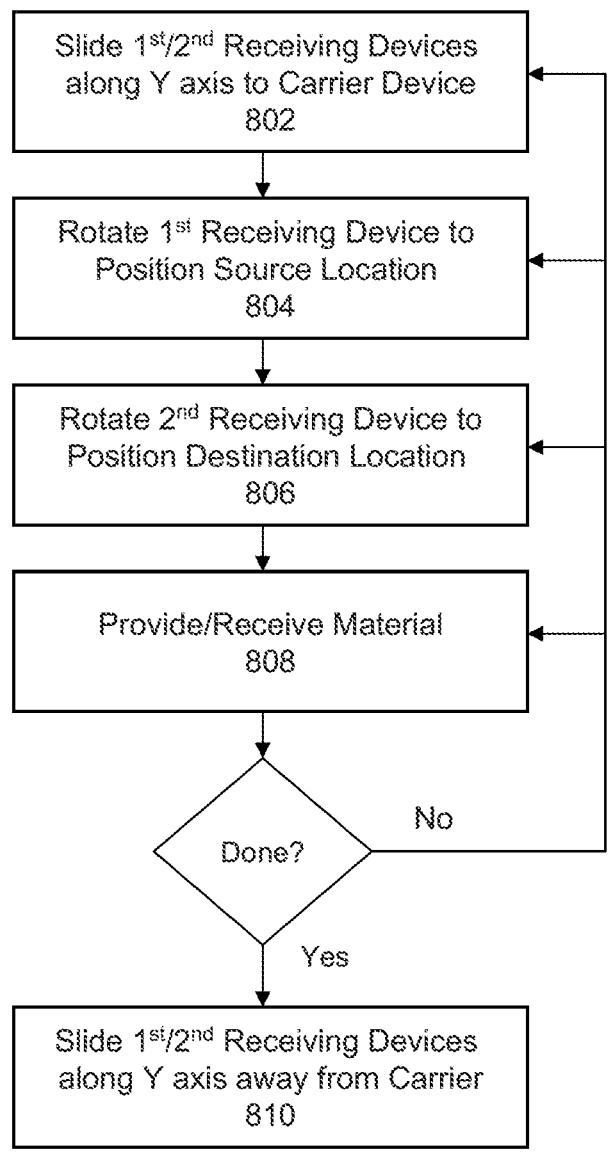
FIG. 8 is a flow diagram providing the method for movement of the carrier devices for material transfer of FIG. 6 in more detail, according to an embodiment of the invention.

Referring now to FIG. 8, there is shown a flow diagram illustrating the moving 602, 610 of the receiving devices 103 in more detail, according to an embodiment of the invention. The method comprises sliding 802 a first and second receiving device 103 along the tracks in the deck 118 to move the receiving devices 103 along a Y axis toward one of the carrier devices 102. The method further includes rotating 804 the first receiving device 103 on the track from 0 degrees to 360 degrees to position the source location (in the container held by the first receiving device 103) directly under the tip 126 of the carrier device 102 for providing the material. The method also includes rotating 806 the second receiving device 103 on the track to position the destination location (in the container held by the second receiving device 103) directly under the tip 126 of one of the carrier devices 102 for receiving the material. In some cases, only one of the receiving devices 103 may need rotation, so one of steps 804 and 806 may be skipped. In addition, the method includes providing/receiving 808 the material to/from the receiving devices 103. If one or both of the receiving device 103 have completed the task for that experiment, that device 103 can then slide 810 along the tracks in the deck 118 away from the carrier devices 102. If either or both of the receiving devices 103 are to move to another location to continue the experimental run, any of steps 802-808 can be repeated. Any of rotating steps 804, 806 and sliding steps 802, 808 may occur simultaneously.

Figure 9:
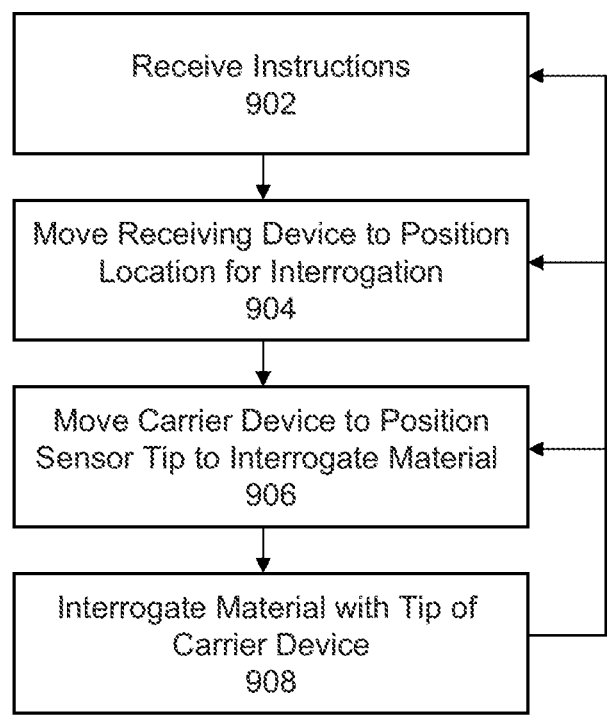
FIG. 9 is a flow diagram providing a method for material interrogation, according to an embodiment of the invention.

Referring now to FIG. 9, there is shown a flow diagram providing a method for material interrogation, according to an embodiment of the invention. As shown in FIG. 9, the method includes a step of receiving 902 instructions for performing an experiment involving interrogating or collecting data about a material from a location in a container. The instructions can be received from a microcontroller or computer system managing the method of material interrogation. Based on these instructions, the carrier device 102 and receiving device 103 are moved around to interrogate the material. Specifically, the method further includes moving 904 at least one receiving device 103 holding a container 202 having the location along at least two axes (e.g., a Y axis and a Theta axis). The moving 904 step can include sliding the receiving device 103 along a track to translate the receiving device 103 toward or away from the carrier device 102 and rotating the device 103 on the track from 0 degrees to 360 degrees to position the location in the container directly under the tip of the carrier device. In addition, the method includes moving 906 a carrier device 102 independently from one or more other carrier devices 102 along at least two axes to position the carrier device 102 for interrogating the material. In one embodiment, the at least two axes of the carrier devices are orthogonal to each other (e.g., an X axis and a Z axis). The moving 906 step can include sliding the device 102 along an X axis to position it in proximity to the receiving device 103 and sliding the tip of the device 102 along a Z axis toward or away from the receiving device 103 to interrogate the material. Furthermore, the method includes interrogating 908 the material, which can include recording physical characteristics or taking an image of the material, among other analyses previously described. Any of steps of FIG. 9 can then be repeated as desired.

While the present teachings are described in conjunction with various embodiments, it is not intended that the present teachings be limited to such embodiments. On the contrary, the present teachings encompass various alternatives, modifications, and equivalents, as will be appreciated by those of skill in the art. Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

What is claimed is:

1. A system for transfer of material from a source location to a destination location comprising:
a hub comprising a stationary base;
a plurality of carrier devices moveably connected to the hub for transferring the material from the source location to the destination location, the plurality of carrier devices comprising a first carrier device and a second carrier device;
a carrier movement mechanism connected to the hub and forming a part of each of the plurality of carrier devices to move each of the plurality of carrier devices independently from each other along at least two first axes, an axis of the at least two first axes being a translation axis parallel to the stationary base;
a plurality of receiving devices moveably connected to the hub, each receiving device of the plurality of receiving devices being configured for holding a container having at least one of the source location or the destination location, the plurality of receiving devices comprising a first receiving device and a second receiving device;
a receiver movement mechanism connected to the hub and forming a part of each of the plurality of receiving devices to move each of the plurality of receiving devices independently from each other along at least two second axes, a first axis of the at least two second axes being a rotation axis perpendicular to the stationary base, a second axis of the at least two second axes being a translation axis parallel to the stationary base; and
a computer system including instructions for the carrier movement mechanism and the receiver movement mechanism to simultaneously coordinate movement of each of (1) the first carrier device and the second carrier device along the at least two first axes and (2) the first receiving device and the second receiving device along the at least two second axes, to positions where the first carrier device and the second carrier device have access to a container that may be held by the first receiving device or the second receiving device.

2. The system of claim 1, wherein the at least two first axes are orthogonal to each other.

3. The system of claim 2, wherein the at least two first axes comprise an X axis and a Z axis.

4. The system of claim 1, wherein the at least two second axes comprise a Y axis orthogonal to an X and a Z axis, and a Theta axis coincident with the Z axis.

5. The apparatus system of claim 1, wherein the carrier movement mechanism is configured for moving the plurality of carrier devices independently from each other along an X axis and along a Z axis, and wherein the receiver movement mechanism is configured for moving the plurality of receiving devices independently from each other and from the plurality of carrier devices along a Y axis and along a Theta axis.

6. The system of claim 1, wherein the receiver movement mechanism is further configured for rotating a receiving device of the plurality of receiving devices from 0 degrees up to 360 degrees in a counterclockwise or a clockwise direction relative to a carrier device of the plurality of carrier devices.

7. The system of claim 1, further comprising:
a transfer probe moveably attached to each carrier device of the plurality of carrier devices; and
a slider connected to the carrier movement mechanism for sliding a transfer probe along a Z axis toward or away from the plurality of receiving devices.

8. The system of claim 7, further comprising a tip connected to each transfer probe for acquiring and depositing the material, wherein each tip is a fixed non-removable tip or a disposable removable tip.

9. The system of claim 1, wherein the hub further comprises:
a deck positioned on the base and under the plurality of carrier devices; and
a plurality of tracks along the deck, wherein the receiver movement mechanism is configured to move at least one receiving device of the plurality of receiving devices along at least one track of the plurality of tracks.

10. The system of claim 9, wherein the receiver movement mechanism comprises:
a plurality of receiver movement sub-mechanisms, one corresponding to each receiving device of the plurality of receiving devices, and wherein each receiver movement sub-mechanism of the plurality of receiver movement sub-mechanisms comprises:
a connector for connecting the each receiver movement sub-mechanism, under the deck and through an opening in the deck, to a corresponding receiving device above the deck on a track of the plurality of tracks;
a slider for sliding the corresponding receiving device along the track; and
a rotator for rotating the corresponding receiving device on the track from 0 degrees up to 360 degrees to position the source location or the destination location directly under a tip of a carrier device of the plurality of carrier devices.

11. The system of claim 7, wherein the material is a liquid, wherein each receiving device of the plurality of receiving devices is configured to hold a microtiter plate, wherein the source location is a well in a first microtiter plate and the destination location is a well in a second microtiter plate, and wherein a liquid aspirator and a liquid dispenser are coupled to a tip of each transfer probe for aspirating the liquid from the well in the first microtiter plate and dispensing the liquid into the well in the second microtiter plate.

12. The system of claim 1, wherein each receiving device of the plurality of receiving devices is configured to hold a microtiter plate, a vial, a tube, a tube rack, a microscope slide, or a microarray.

13. The system of claim 1, wherein the plurality of carrier devices comprises at least one component selected from the group consisting of: a piston-type aspirator/dispenser, an air displacement aspirator/dispenser, an acoustic aspirator/dispenser, a pin tool, and an extraction tool.

14. The system of claim 1, wherein the plurality of receiving devices comprises at least four receiving devices, and wherein the receiver movement mechanism is further configured for moving the at least four receiving devices independently from one another along a Y axis and independently from one another along a Theta axis.

15. The system of claim 1, wherein the plurality of carrier devices comprises at least four carrier devices and wherein the carrier movement mechanism is configured for moving the at least four carrier devices independently from one another along an X axis and independently from one another along a Z axis.

16. The system of claim 1, wherein each receiving device of the plurality of receiving devices is configured to hold a 1536-well microtiter plate.

17. The system of claim 1, wherein a carrier device of the plurality of carrier devices further comprises a sensor.

18. The system of claim 17, wherein the sensor is a sensor selected from the group consisting of: an electrochemical sensor, a temperature sensor, a capacitance sensor, a biosensor, a surface plasmon resonance sensor, a conductivity sensor, a calorimeter, a microspectrophotometer sensor, an ionizing radiation sensor, a voltage sensor, a humidity sensor, an electric field sensor, an oxygen sensor, a humidity sensor, an optical sensor, and a camera.

* * * * *